(12) United States Patent
Mankos

(10) Patent No.: US 6,878,937 B1
(45) Date of Patent: Apr. 12, 2005

(54) PRISM ARRAY FOR ELECTRON BEAM INSPECTION AND DEFECT REVIEW

(75) Inventor: Marian Mankos, Palo Alto, CA (US)

(73) Assignee: KLA-Tencor Technologies Corporation, Milpitas, CA (US)

(*) Notice: Subject to any disclaimer, the term of this patent is extended or adjusted under 35 U.S.C. 154(b) by 0 days.

(21) Appl. No.: 10/775,646

(22) Filed: Feb. 10, 2004

(51) Int. Cl.$^7$ ............................................. G01N 23/225
(52) U.S. Cl. ...................... 250/310; 250/306; 250/307
(58) Field of Search ............................... 250/306, 307, 250/310, 305

(56) References Cited

U.S. PATENT DOCUMENTS

| | | | |
|---|---|---|---|
| 5,319,207 A | | 6/1994 | Rose et al. |
| 6,586,733 B1 | * | 7/2003 | Veneklasen et al. ........ 250/306 |
| 6,803,571 B1 | * | 10/2004 | Mankos et al. ............. 250/310 |
| 6,803,572 B2 | * | 10/2004 | Veneklasen et al. ........ 250/310 |

OTHER PUBLICATIONS

R.M. Tromp "Low–energy electron microscopy", IBM J. Res. Develop., Jul. 2000, pp. 503–516, vol. 44, No. 4.
V. Kolarik, et al. "Close packed prism arrays for electorn microscopy", Optik 87, No. 1 (1991), pp. 1–12.
H. Rose, et al. "Outline of a versatile corrected LEEM", Optik 92, No. 1 (1992), pp. 31–44.

* cited by examiner

*Primary Examiner*—Nikita Wells
*Assistant Examiner*—Johnnie L Smith, II
(74) *Attorney, Agent, or Firm*—Okamoto & Benedicto LLP

(57) ABSTRACT

One embodiment disclosed relates to an apparatus for inspecting a substrate using charged particles. The apparatus includes illumination optics, objective optics, projection optics, and a beam separator. The beam separator is configured to receive the incident beam from the illumination optics and bend the incident beam towards the objective optics, and also to receive the scattered beam from the objective optics and bend the scattered beam towards the projection optics. The beam separator comprises a magnetic prism array including a central magnetic sector, inner magnetic sectors outside the central sector, and outer magnetic sectors outside the inner sectors. Each of the inner and outer sectors may be configured to have its field strength independently adjustable for alignment and focusing purposes.

20 Claims, 3 Drawing Sheets

US 6,878,937 B1

PRISM ARRAY FOR ELECTRON BEAM INSPECTION AND DEFECT REVIEW

BACKGROUND OF THE INVENTION

1. Field of the Invention

The present invention relates to apparatus and methods for inspection or review of semiconductor wafers and masks.

2. Description of the Background Art

The generation of electron optical imaging systems which utilize electrons reflecting of the surface of a flat substrate are complicated when compared to conventional straight-axis electron beam systems. This situation is present because the electron beam passes twice through one or more electron lenses. A design including a plurality of lenses arranged along one straight axis is therefore not practically feasible, and a beam separator is needed to split the incoming and outgoing beams.

A conventional method of low-energy electron microscopy utilizes a prism with a single shaped magnetic field as a beam separator. For example, see E. Bauer, "Low energy electron microscopy," Rep. Prog. Phys. 57 (1994), p. 895. However, such a beam separator disadvantageously has uncorrected astigmatism.

This deficiency may be compensated for by using a corrected prism design. See V. Kolarik et al., "Close packed prism arrays for electron microscopy," Optik 87 No. 1 (1991), p. 1; H. Rose et al., "Outline of a versatile corrected LEEM," Optik 92 No. 1 (1992), p. 31; and U.S. Pat. No. 5,319,207 to Rose et al. (the Rose et al. patent).

For example, FIGS. 1, 2a, and 2b of the Rose et al. patent depict a design that utilizes two uniform fields to reduce astigmatism in the imaging. However, that design is problematic and disadvantageous in that a very high level of accuracy of the inner and outer sector lengths is required in order to achieve stigmatic imaging.

As another example, FIG. 6 of the Rose et al. patent depicts a design that uses opposed uniform fields. However, that design has a complex geometry that is difficult to fabricate and is dispersion free, which in some cases is undesirable.

SUMMARY

One embodiment of the invention pertains to an apparatus for inspecting a substrate using charged particles. The apparatus includes illumination optics, objective optics, projection optics, and a beam separator. The beam separator is configured to receive the incident beam from the illumination optics and bend the incident beam towards the objective optics, and also to receive the scattered beam from the objective optics and bend the scattered beam towards the projection optics. The beam separator comprises a magnetic prism array including a central magnetic sector, inner magnetic sectors outside the central sector, and outer magnetic sectors outside the inner sectors. Each of the inner and outer sectors may be configured to have its field strength independently adjustable for alignment and focusing purposes.

Another embodiment of the invention pertains to a beam separator for use in an electron beam inspection apparatus. The beam separator includes a central magnetic sector, inner magnetic sectors outside the central magnetic sector; and outer magnetic sectors outside the inner magnetic sectors. The central magnetic sector generates a first magnetic field of a first field strength, each inner magnetic sector generates a second magnetic field of a second field strength, and each outer magnetic sector generates a third magnetic field of a third field strength.

Another embodiment of the invention pertains to a method of inspecting a substrate using charged particles. An incident charged-particle beam is generated, bent through a first outer magnetic sector, a first inner magnetic sector, a central magnetic sector, a second inner magnetic sector, and a second outer magnetic sector, and focused onto a substrate. A reflected charged-particle beam is received, bent through the second outer magnetic sector, the second inner magnetic sector, the central magnetic sector, a third inner magnetic sector, and a third outer magnetic sector, and projected to a detection system.

Another embodiment of the invention pertains to a low-energy electron beam inspection apparatus. The apparatus includes means for generating an incident charged-particle beam, means for decelerating and focusing the incident beam to a substrate, means for accelerating and refocusing a reflected charged-particle beam, means for projecting the reflected beam to a detection system, and a magnetic prism array. The magnetic prism array is configured to bend the incident beam through a first outer magnetic sector, a first inner magnetic sector, a central magnetic sector, a second inner magnetic sector, and a second outer magnetic sector. The magnetic prism array is further configured to bend the reflected beam through the second outer magnetic sector, the second inner magnetic sector, the central magnetic sector, a third inner magnetic sector, and a third outer magnetic sector.

DETAILED DESCRIPTION

Figure 1:
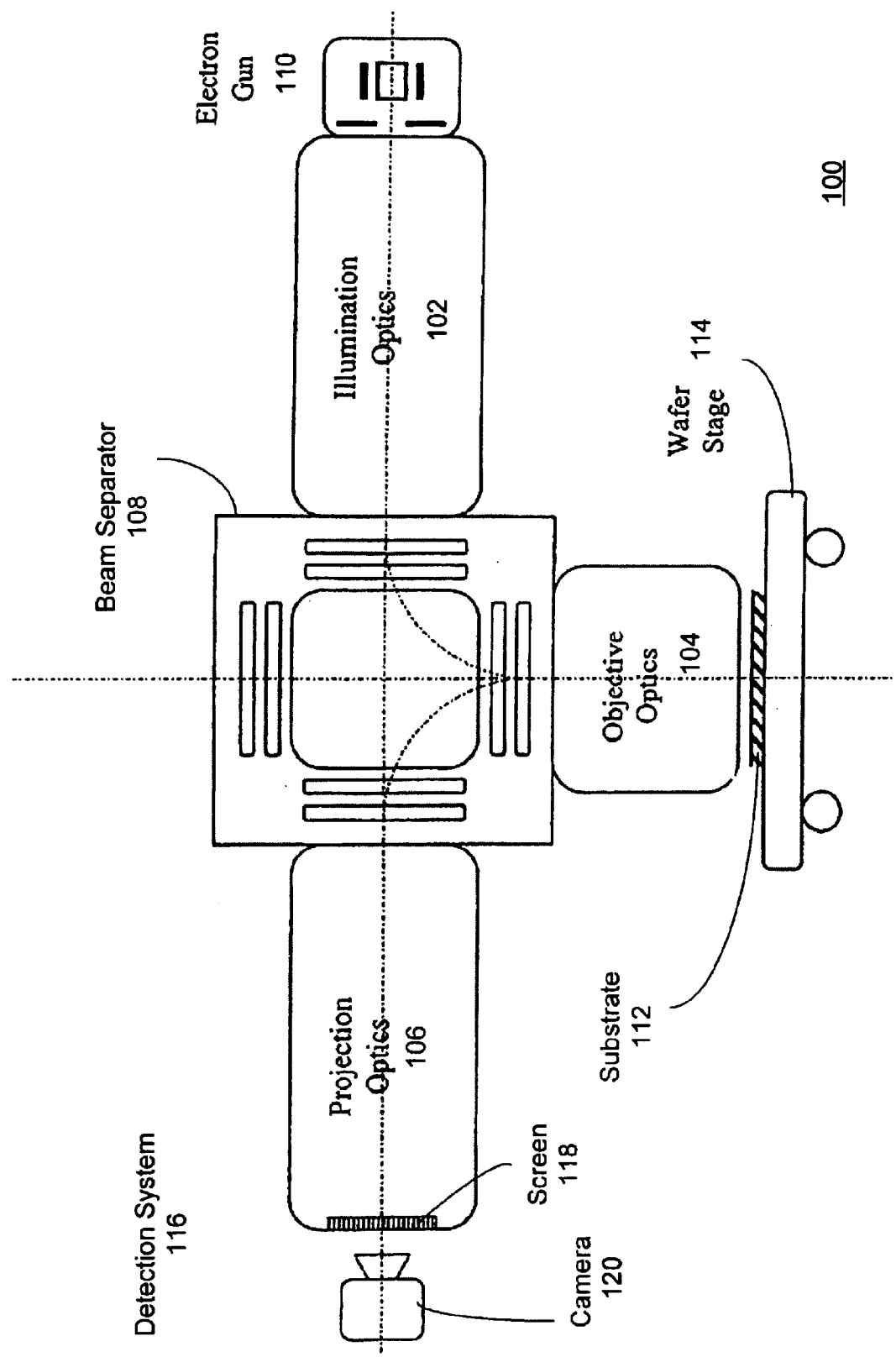
FIG. 1 is a schematic diagram depicting an apparatus for inspecting a substrate using charged particles in accordance with an embodiment of the invention.

FIG. 1 is a schematic diagram depicting an apparatus 100 for inspecting a substrate using charged particles in accordance with an embodiment of the invention. The apparatus 100 includes an illumination subsystem 102, an objective subsystem 104, a projection subsystem 106, and a beam separator 108. The beam separator 108 is coupled to and interconnects the illumination subsystem 102, the objective subsystem 104, and the projection subsystem 106.

The illumination subsystem (illumination optics) 102 is configured to receive and collimate charged particles from a charged-particle source. In a preferred embodiment, the charged particles comprise electrons, and the source comprises an electron gun 110. In a preferred embodiment, the illumination subsystem 102 comprises an arrangement of magnetic and/or electrostatic lenses configured to focus the charged particles from the source so as to generate an incident charged-particle beam. The specific details of the arrangement of lenses depend on specific parameters of the apparatus and may be determined by one of skill in the pertinent art.

The beam separator 108 is configured to receive the incident beam from the illumination subsystem 102 and to bend or deflect the incident beam by 90 degrees into the objective subsystem 104. In a preferred embodiment, the beam separator 108 comprises a magnetic prism array including a central magnetic section, an inner magnetic section outside the central section, and an outer magnetic section outside the inner section. The preferred embodiment of the beam separator 108 is described further below in relation to FIGS. 2 and 3.

The objective subsystem (objective optics) 104 is configured to receive the incident beam from the beam separator 108 and to decelerate and focus the incident beam onto the substrate 112. The incident beam onto the substrate 108 causes reflection and/or emission of a scattered beam of charged particles. The scattered beam comprises a two-dimensional image of the illuminated area of the substrate 112.

The objective optics 104 is further configured to re-accelerate the scattered beam and to refocus the two-dimensional image of the substrate area. In a preferred embodiment, the objective optics 104 comprises an arrangement of magnetic and/or electrostatic lenses configured to focus and decelerate the incident beam to the substrate 112 and to retrieve and re-accelerate the scattered beam from the substrate 112.

In one implementation, to accomplish the deceleration and re-acceleration, the substrate may be maintained at a negative high voltage potential close to that of the incident beam source while the objective optics is at ground potential. In an alternative arrangement, the substrate (and source) may be at ground potential and the objective optics (and other components) at a high voltage. Further specific details of the arrangement of lenses depend on specific parameters of the apparatus and may be determined by one of skill in the pertinent art.

The beam separator 108 is configured to receive the scattered beam from the objective optics 104 and to bend the scattered beam towards the projection subsystem 106. A preferred embodiment of the beam separator 108 is described further below in relation to FIGS. 2 and 3.

The projection subsystem (optics) 106 is configured to receive the scattered beam from the beam separator 108 and to magnify and project the scattered beam onto a detector 116. In this way, a magnified two-dimensional image of the illuminated substrate area is obtained. In one embodiment, the detector 116 may comprise a phosphorescent screen 118 and a camera 120 as depicted. In another embodiment, the detector 116 may include a charge-coupled device (CCD) array.

Figure 2:
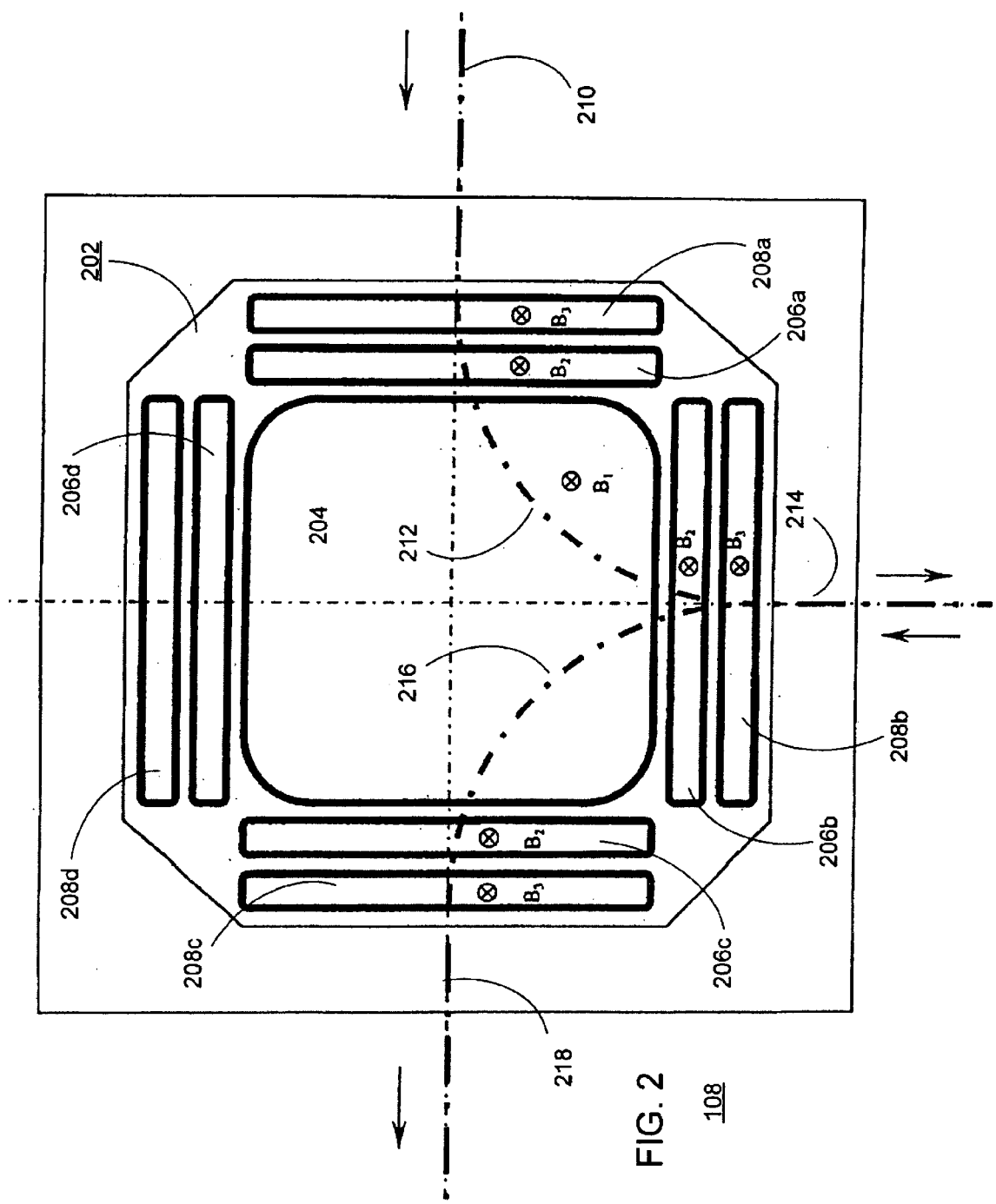
FIG. 2 is a schematic diagram depicting the beam separator in further detail in accordance with an embodiment of the invention.

FIG. 2 is a schematic diagram depicting the beam separator 108 in further detail in accordance with an embodiment of the invention. The beam separator 108 comprises a magnetic prism array 202 that is configured advantageously. The array 202 comprises a central sector 204, an inner section 206 configured outside of and around the central sector 204, and an outer section 206 configured outside of and around the inner section 206.

In the embodiment illustrated, the inner section 206 comprises multiple inner sectors (206a, 206b, 206c, and 206d), and the outer section 208 comprises multiple outer sectors (208a, 208b, 208c, and 208d). In particular, the central sector 204 is surrounded by an inner 206 an outer 208 sector along each axis (for a total of 9 sectors in this instance). Each of the sectors (including the central sector 204, the multiple inner sectors 206, and the multiple outer sectors 208) generates a substantially uniform magnetic field of a different strength and affects a different trajectory portion. As illustrated, during each 90-degree deflection, the pertinent charged particle beam passes through an outer sector, an inner sector, the central sector, another inner sector, and another outer sector. The lengths of the affected trajectory portion in the inner and outer sectors are significantly shorter than that in the central sector.

The incident charged-particle beam from the illumination optics 102 is received on an initial trajectory 210 as depicted in FIG. 2. When the incident beam enters the prism array 202, it traverses the magnetic field of strength $B_3$ produced by the first outer sector 208a which faces the illumination optics 102. Next, the incident beam traverses the magnetic field of strength $B_2$ produced by the first inner sector 206a. Next, the incident beam travels across the magnetic field of strength $B_1$ produced by the central sector 204.

As the incident beam traverses these magnetic fields, a force proportional to the magnetic field strengths acts on the charged particles in a direction perpendicular to their trajectory (i.e. perpendicular to their velocity vectors). In particular, as the incident beam traverses the outer. Inner, and central sectors, its trajectory 212 is bent towards the side of the magnetic prism array 202 that faces the objective optics 104.

The incident beam exits the central sector 204 and enters the magnetic field of strength $B_2$ produced by the second inner sector 206b. After traversing the second inner sector 206b, the incident beam traverses the magnetic field of strength $B_3$ produced by the second outer sector 208b. The second inner and outer sectors further bend the trajectory of the incident beam. After passing through these two sectors, the incident beam is on a trajectory 214 heading into the objective optics 104.

The objective optics 104 focuses and decelerates the incident charged-particle beam such that it impinges upon an area being inspected on the substrate 112. Scattered charged particles are generated as a result of the impingement. In a preferred embodiment, the scattered particles comprise reflected, secondary emission or backscattered electrons. The scattered particles form a scattered beam which is re-accelerated by the objective optics 104 as it travels away from the substrate 112.

The scattered beam exits the central sector 104 and enters the magnetic field of strength $B_3$ produced by the second outer sector 208b. After traversing the second outer sector 208b, the scattered beam traverses the magnetic field of strength $B_2$ produced by the second inner sector 206b. After passing through these two sectors, the scattered beam traverses the central sector 204.

As the scattered beam traverses these magnetic fields, a force proportional to the magnetic field strengths acts on the charged particles in a direction perpendicular to their trajectory (i.e. perpendicular to their velocity vectors). In particular, as the scattered beam traverses the outer, inner, and central sectors, its trajectory 216 is bent towards the side of the magnetic prism array 202 that faces the projection optics 106.

The scattered beam exits the central sector 204 and enters the magnetic field of strength $B_2$ produced by the third inner sector 206c. After traversing the third inner sector 206c, the scattered beam traverses the magnetic field of strength $B_3$ produced by the third outer sector 208c. The third inner and outer sectors further bend the trajectory of the scattered beam. After passing through these two sectors, the scattered beam is on a trajectory 218 heading into the projection optics 106.

As described above in relation to FIG. 1, the projection optics 106 is configured to receive the scattered beam and to project the scattered beam onto a detection system 116. In this way, a magnified two-dimensional image of the area being inspected is obtained.

While the prism array 202 includes a fourth inner sector 206d and a fourth outer sector 206d, these are not utilized to affect the charged-particle beam trajectories. Hence, they are optional to include in the prism array 202.

One aspect of the present invention pertains to the advantageous use of the double (both outer 208 and inner 206) sector layer surrounding the central sector 204. In contrast, the conventional magnetic prism array includes only a single sector layer surrounding the central sector.

Figure 3:
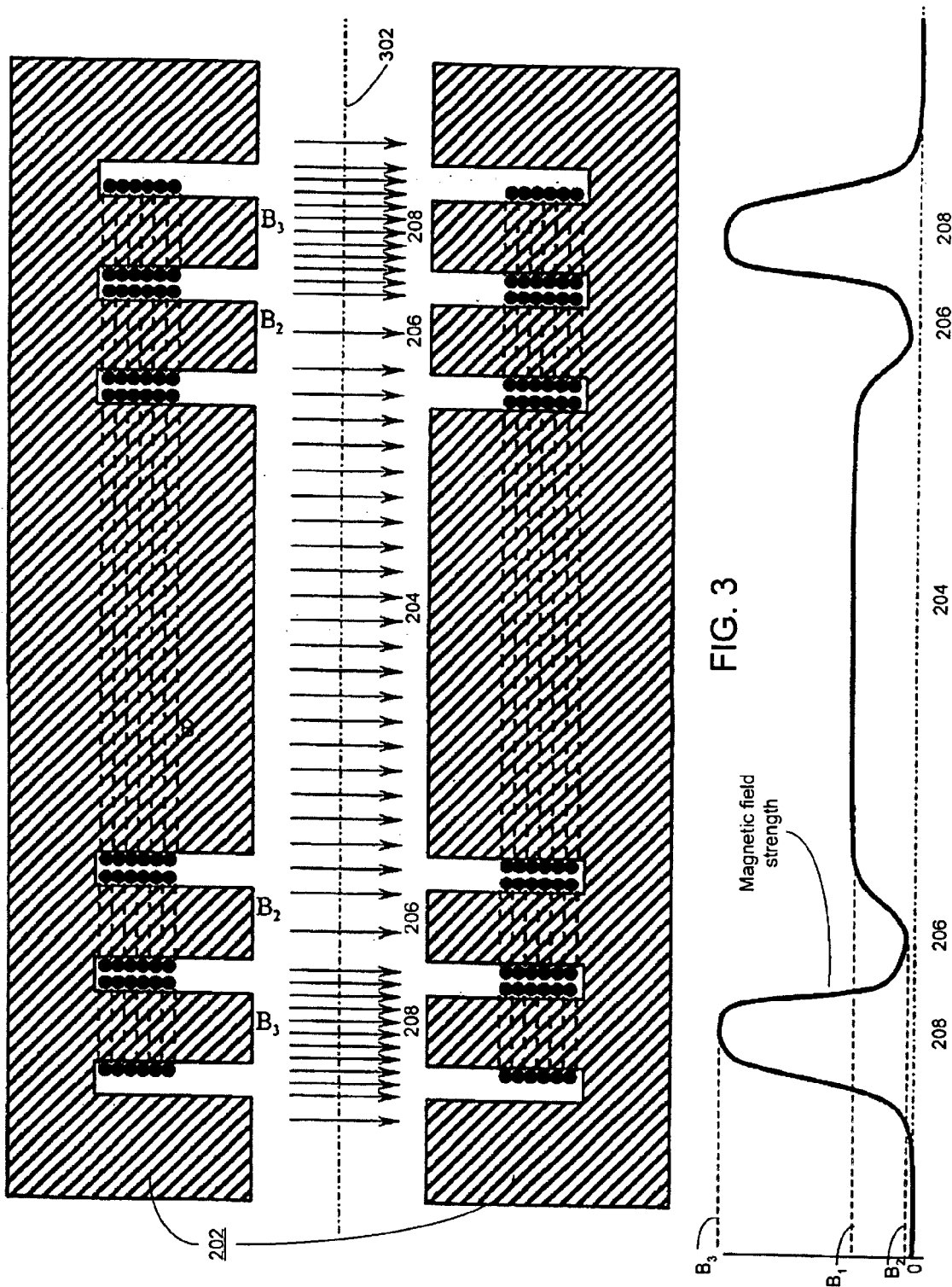
FIG. 3 is an illustration depicting a cross-sectional view of the magnetic prism array and magnetic field strengths therein in accordance with an embodiment of the invention.

FIG. 3 is an illustration depicting a cross-sectional view of the magnetic prism array and magnetic field strengths therein in accordance with an embodiment of the invention. The figure illustrates the electrical coils (shown as dots with dashed lines therebetween) utilized for the electromagnets in the array. Current is run through the coils to generate the magnetic fields, where the strength of the magnetic field generated is proportional to the current. Since FIG. 3 is a cross section, only two of the three inner/outer sector pairs are shown. The third (not shown) pair is similarly configured to generate magnetic fields. Below the cross section, a graph depicting the magnetic field strength as a function of the position along the mid-line 302 through the prism array is shown.

In accordance with a preferred embodiment, the magnetic field strength in each of the outer sectors 208 is a relatively high level of $B_3$. In contrast, the magnetic field strength in each of the inner sector 206 is a relatively low level of $B_2$. The magnetic field strength in the central sector 204 is at an intermediate level of $B_1$. These magnetic field strengths are determined by the chosen excitations of the coils (i.e. the electrical current run through the coils).

The excitations of the coils are selected such that the prism array 202 acts as a thick round lens along the curved axes through it and bends the charged-particle beams by 90 degrees, where the trajectories illustrated in FIG. 2 are along the curved axes. As such, the prism 202 may be set to image stigmatically in both the image and diffraction planes while deflecting the charged-particle beams by 90 degrees. The stigmatic focusing and round lens behavior substantially simplifies the set-up, alignment and operation of the apparatus.

Now consider that the central sector 204 deflects a beam trajectory by an angle of $\phi_1$, each inner sector 206 deflects the beam by an angle of $\phi_2$, and each outer sector 208 deflects the beam by an angle of $\phi_3$. The angle $\phi_1$ is due to $B_1$ and the length of the path through the central sector 204. The angle $\phi_2$ is due to $B_2$ and the length of the path through an inner sector 206. The angle $\phi_3$ is due to $B_3$ and the length of the path through an outer sector 208.

An advantageous aspect of the invention relates to the following. For a given magnetic field strength $B_1$, there is a range of magnetic field strengths for $B_2$ and $B_3$ such that the total deflection angle $\phi_1+2\phi_2+2\phi_3$ equals 90 degrees. In other words, the ratio of $B_2/B_3$ is variable. For example, $B_3$ may be decreased and $B_2$ increased such that the 90 degree total deflection is maintained. Similarly, $B_3$ may be increased and $B_2$ decreased such that the 90 degree total deflection is maintained.

The feature of having two separate and independently-controllable coils generating flux densities $B_2$ and $B_3$ in each arm of the magnetic prism array 202 allows for the flexible variation in the effective lengths of the center and outer fields, while maintaining the stigmatic focusing characteristic. In a preferred embodiment, each of the inner 206 and outer 208 sectors independently controllable from each other (such that two inner sectors need not have the exact same magnetic field strengths, and two outer sectors also need not have the exact same magnetic field strengths). This enables the invented prism array 202 to be "tuned" to adjust for potential machining and/or calculation errors, such that a desired imaging condition and alignment is obtainable. In contrast, the conventional magnetic prism array with only one sector per arm cannot compensate for machining and/or calculation errors without adversely affecting the stigmatic focusing behavior of the prism or the alignment of the beam in the objective and/or projection optics.

As a further advantage, the two independent prism sectors in each arm (quadrant) simplify the necessary design and machining of the prism sectors. Because of the flexibility provided by the two independent sectors, the sectors may be designed with straight edges and 90 degree angles, without any curved edges or cuts at arbitrary angles.

As described in detail above, an embodiment of the present invention relates to an electron inspection system with parallel imaging of semiconductor substrates and masks using low-energy electron microscopy. One aspect of the invention pertains to a novel and advantageously designed magnetic prism array having one central sector and two independent sectors in each quadrant, an example of which is depicted in FIG. 1. This prism array advantageously enables tuning to an optimal imaging condition while compensating for machining and simulation errors. The inspection system utilizes the above-described magnetic prism separator to achieve improved performance.

While the above-described embodiment includes two magnetic sectors per arm or quadrant of the prism array, more than two sectors per arm may also be utilized to achieve the same effect.

The above-described diagrams are not necessarily to scale and are intended be illustrative and not limiting to a particular implementation. The above-described invention may be used in an automatic inspection or review system and applied to the inspection or review of optical or X-ray masks and similar substrates in a production environment.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An apparatus for inspecting a substrate using charged particles, the apparatus comprising:

an illumination subsystem configured to generate an incident charged-particle beam;

an objective subsystem configured to receive the incident beam, to focus the incident beam onto the substrate, and to retrieve a scattered beam from the substrate;

a projection subsystem configured to receive the scattered beam and to project the scattered beam onto a detector; and a beam separator coupled to and interconnecting the illumination subsystem, the objective subsystem, and the projection subsystem;

wherein the beam separator is configured to receive the incident beam from the illumination subsystem, bend the incident beam towards the objective subsystem, receive the scattered beam from the objective subsystem, and bend the scattered beam towards the projection subsystem; and wherein the beam separator comprises a magnetic prism array including a central magnetic sector, inner magnetic sectors positioned outside the central sector, and outer magnetic sectors positioned outside the inner magnetic sectors.

2. The apparatus of claim 1, wherein the central sector generates a first magnetic field of a first field strength, each inner sector generates a second magnetic field of a second field strength, and each outer sector generates a third magnetic field of a third field strength.

3. The apparatus of claim 2, wherein the first magnetic field causes beam deflection of a first angle, the second magnetic field causes beam deflection of a second angle, and the third magnetic field causes beam deflection of a third angle.

4. The apparatus of claim 3, wherein the first angle, twice the second angle, and twice the third angle sum to a bending angle of approximately ninety degrees.

5. The apparatus of claim 4, wherein each of the inner and outer sectors is configured to have its field strength independently adjustable.

6. The apparatus of claim 5, wherein the apparatus comprises a low-energy electron microscope, wherein the incident beam comprises incident electrons, and wherein the scattered beam comprises reflected electrons.

7. The apparatus of claim 1, wherein the inner sectors are configured with straight edges and right angles.

8. The apparatus of claim 1, wherein the outer sectors are configured with straight edges and right angles.

9. The apparatus of claim 1, wherein the magnetic prism array is configured such that the incident beam passes through a first outer sector, a first inner sector, the central section, a second inner sector, and a second outer sector.

10. The apparatus of claim 9, wherein the magnetic prism array is further configured such that the scattered beam passes through the second outer sector, the second inner sector, the central section, a third inner sector, and a third outer sector.

11. A beam separator for use in an electron beam inspection apparatus, the beam separator comprising:

a central magnetic sector;

inner magnetic sectors outside the central magnetic sector; and outer magnetic sectors outside the inner magnetic sectors;

wherein the central magnetic sector generates a first magnetic field of a first field strength, each inner magnetic sector generates a second magnetic field of a second field strength, and each outer magnetic sector generates a third magnetic field of a third field strength.

12. The beam separator of claim 11, wherein the first magnetic field causes beam deflection of a first angle, the second magnetic field causes beam deflection of a second angle, and the third magnetic field causes beam deflection of a third angle, and wherein the first angle, twice the second angle, and twice the third angle sum to a bending angle of approximately ninety degrees.

13. The beam separator of claim 12, wherein each of the inner and outer sectors is configured to have its field strength adjusted independently.

14. A method of inspecting a substrate using charged particles, the method comprising:

generating an incident charged-particle beam;

bending the incident beam through a first outer magnetic sector, a first inner magnetic sector, a central magnetic sector, a second inner magnetic sector, and a second outer magnetic sector;

focusing the incident beam to a substrate;

retrieving a reflected charged-particle beam;

bending the reflected beam through the second outer magnetic sector, the second inner magnetic sector, the central magnetic sector, a third inner magnetic sector, and a third outer magnetic sector;

projecting the reflected beam to a detection system.

15. The method of claim 14, wherein the incident beam is bent through an angle of approximately ninety degrees.

16. The method of claim 15, wherein the reflected beam is bent through an angle of approximately ninety degrees.

17. The method of claim 16, wherein field strengths of the magnetic sectors are independently adjustable.

18. The method of claim 17, wherein varying magnetic field strengths of the inner magnetic sectors varies an effective length of the central and outer magnetic sectors.

19. The method of claim 18, wherein the charged particles comprise electrons.

20. A low-energy electron beam inspection apparatus, the apparatus comprising:

means for generating an incident charged-particle beam;

means for decelerating and focusing the incident beam to a substrate;

means for accelerating and refocusing a reflected charged-particle beam;

means for projecting the reflected beam to a detection system to form a two-dimensional image; and a magnetic prism array configured to bend the incident beam through a first outer magnetic sector, a first inner magnetic sector, a central magnetic sector, a second inner magnetic sector, and a second outer magnetic sector, and further configured to bend the reflected beam through the second outer magnetic sector, the second inner magnetic sector, the central magnetic sector, a third inner magnetic sector, and a third outer magnetic sector.

* * * * *